United States Patent
Formenti

(10) Patent No.: US 7,763,864 B2
(45) Date of Patent: Jul. 27, 2010

(54) RADIATION TREATMENT TABLE AND METHOD FOR PRONE BREAST RADIATION TREATMENT

(75) Inventor: Silvia C. Formenti, New York, NY (US)

(73) Assignee: New York University, New York, NY (US)

(*) Notice: Subject to any disclaimer, the term of this patent is extended or adjusted under 35 U.S.C. 154(b) by 982 days.

(21) Appl. No.: 11/278,922

(22) Filed: Apr. 6, 2006

(65) Prior Publication Data

US 2007/0033735 A1 Feb. 15, 2007

Related U.S. Application Data

(60) Provisional application No. 60/669,046, filed on Apr. 6, 2005.

(51) Int. Cl.
*A61B 6/04* (2006.01)
*G21K 5/08* (2006.01)

(52) U.S. Cl. ............... 250/453.11; 250/492.3; 600/407; 378/37; 378/209; 378/205; 5/601; 5/632; 128/845

(58) Field of Classification Search ............ 250/492.3, 250/453.11; 600/407; 378/37, 205, 209; 5/601, 632; 128/845
See application file for complete search history.

(56) References Cited

U.S. PATENT DOCUMENTS

| 3,165,630 | A | * | 1/1965 | Bielat et al. | 378/37 |
| 5,564,438 | A | | 10/1996 | Merchant | |
| 6,883,194 | B2 | * | 4/2005 | Corbeil et al. | 5/601 |
| 7,492,858 | B2 | * | 2/2009 | Partain et al. | 378/37 |

* cited by examiner

*Primary Examiner*—Jack I Berman
(74) *Attorney, Agent, or Firm*—Fish & Richardson P.C.

(57) ABSTRACT

A method and device for accurately and reproducibly positioning a woman's breast to receive radiation while the woman is positioned in a prone, face-down position upon a radiation treatment table are disclosed. The treatment table is useable with radiation accelerator tables of existing linear accelerator machines. The treatment table includes a generally flat patient support surface having an opening that allows the patient's breast to fall dependently below the support surface through the opening yet remain above the radiation accelerator table such that the breast can be irradiated for therapy or treatment. The platform further includes a head positioning device connected to the support surface such that a woman's head can be placed in the positioning device while she lies in the prone position and such that one or both of her breasts can be accurately and reproducibly positioned for treatment through the opening. The platform may include memory foam for achieving reproducible positioning from patient to patient.

14 Claims, 14 Drawing Sheets

RADIATION TREATMENT TABLE AND METHOD FOR PRONE BREAST RADIATION TREATMENT

FIELD OF INVENTION

The present invention relates generally to a method and device for accurately positioning a woman's breast to receive radiation treatment or therapy while the woman is positioned in a prone, face-down position upon a radiation treatment table.

BACKGROUND OF THE INVENTION

Each year, over a hundred thousand new cases of breast cancer are discovered in women living in the United States. A large percentage of these cases will result in fatalities. One of the most generally accepted methods for treating breast cancer is a lumpectomy, followed by uniform dosage of radiation treatment throughout the breast when cancerous cells remain following surgery. In implementing this method of treatment, it is important to ensure that the radiation received by the breast tissue being treated is uniformly received; due to the detrimental effects of radiation, it is also important to minimize the radiation received by surrounding areas of the body.

Patients treated with radiation therapy often experience varying effects from the radiation treatments. One factor of considerable importance is a patient's body-shape. Certain women, such as those with large, pendulous or irregular shaped breasts, are known to be particularly susceptible to increased toxicities from radiation treatment and poor cosmetic outcomes.

Radiation treatments are most typically carried out with the patient in one of two positions—the supine (face-up) position, or the decubitus (side) position. Both positions have certain advantages and disadvantages. While the supine position is considered more reproducible for providing treatment, particularly with respect to women with large or irregularly shaped breasts, this position results in greater irradiation to surrounding areas such as the lungs and heart and it requires the use of non-homogeneous dose distributions. This is because the transverse displacement of breast tissue over the anterior chest wall that results when a patient is placed in this position creates a large separation resulting in non-uniformity in the dose distribution and the irradiation of large volumes of lung and heart. In order to minimize these problems in women with large or irregularly shaped breasts, when treatment is carried out in the supine position, various modifications to the traditional treatment technique are required. Such modifications include the use of wedge filters, high-energy photon beams, beam-spoilers and bolus.

When used with women with large or irregularly shaped breasts, the decubitus technique is performed with the breast tissue compressed to a greater thickness and, as a result, achieves a more homogeneous dose distribution. However, the decubitus technique requires meticulous patient positioning and protection of the contra-lateral breast; it is also less reproducible and lacks the flexibility that supine position treatment offers.

As an alternative to these more commonly used techniques, it has been determined that the prone position can be used to overcome the limitations of treating women with large or irregularly shaped breasts using the supine and decubitus techniques. The prone position combines the advantage of the decubitus position in providing a homogeneous dose distribution with the reproducibility of the supine position. Use of the prone position also provides several additional notable advantages. Specifically, prone treatment optimizes the shape of the breast with regard to the chest wall for treatment and minimizes the volume of normal tissue (such as the heart, lungs, chest wall and contra-lateral breast tissue) irradiated within the radiation therapy portal during breast treatment. Importantly, various recent studies have concluded that high dose radiation regions are notably reduced for women with large or irregularly shaped breasts using the prone position.

The use of the prone position can not be accomplished using unmodified accelerator tables of traditional linear accelerator machines. These tables have a uniform, flat supporting surface on which the patient is placed for treatment. It will be appreciated by those skilled in the art and familiar with breast radiation therapy equipment, that prone breast treatment can not be performed on accelerator machines of this type without the use of an elevated platform or some other modification because the vertical height adjustment of the accelerator table is limited such that it will not allow the transmission of beam portals underneath the patient supporting surface. Furthermore, the presence of metallic frames at the edges of the patient supporting surface prevents and otherwise interferes with laterally directed radiation portals to a breast suspended from the prone position. There is also no way for the accelerator head to be positioned to irradiate one particular breast without irradiating entire surrounding areas as well. Therefore, in order to properly treat the breast tissue, some modification to, or additional equipment to be used with the traditional accelerator table is required. Modifying the accelerator table itself would be very expensive and difficult to accomplish. Instead, other approaches have focused on providing additional equipment to use in conjunction with the accelerator table.

One such approach known in the art to accomplish breast radiation treatment for a patient in a prone position using a traditional linear accelerator is by placing an elevated therapy platform on top of the linear accelerator table. For example, U.S. Pat. No. 5,564,438, the contents of which are incorporated herein by reference, describes an elevated platform positioned upon a radiation accelerator table of a radiation therapy accelerator machine. The platform described in this patent includes an elevated top surface with an opening through which the breast to be irradiated is inserted to hang freely and pendulously through the platform in an open space treatment field over the top of the accelerator table. Using the elevated table having an opening for the breast, this system attempts to isolate the breast tissue to be irradiated from the rest of the body.

However, this system (and other known systems) have several important limitations. For example, the system described in the '438 Patent does not provide a way to reproducibly position the patient's breast in the opening for treatment.

SUMMARY OF THE INVENTION

The present invention overcomes these and other disadvantages of methods and apparatuses previously used to provide prone radiation treatment or therapy to breast tissue. The treatment table allows a female patient to be comfortably, reproducibly and repeatedly positioned for purposes of radiation treatment or therapy. The treatment table allows irradiation of all breast sizes and irradiation from any direction. The treatment table is useable with and securely fastenable to the radiation accelerator table of existing radiation therapy linear accelerator machines. The table is suitable for use with CT and MRI imaging and is constructed in shape and material so that it will not interfere with these, or other imaging modalities.

In accordance with one aspect of the invention, there is provided a method for reproducibly positioning a female patient's breast to receive radiation. The method includes the steps of: (i) positioning a patient in a prone position upon a positioning platform, the positioning platform including: (a) a patient support surface elevated above a linear accelerator table, the patient support surface having at least one opening through which a breast may hang downwardly toward the linear accelerator table, (b) a platform support having at least one vertical support having a lower end adapted to be secured to the linear accelerator table and having an upper end secured to the patient support surface, and (c) a head positioning device; (ii) placing the patient's head in the head positioning device such that at least one of the patient's breasts is positioned to hang downwardly through the opening and below said patient support surface to receive radiation; (iii) positioning a radiation source relative to the patient's breast; and (iv) irradiating the breast.

In accordance with another aspect of the invention, there is provided a radiation treatment table having: (i) a generally flat patient support surface, the surface having an opening to allow a woman's breast to hang down through the opening and below the patient support surface to receive radiation when a woman is placed on the patient support surface in a prone position; (ii) a platform support connected to the patient support surface, the platform support having at least one vertical support, the at least one vertical support having an upper end coupled to the patient support surface and having a lower end adapted to be secured to a linear accelerator table; and (iii) a head positioning device attachable to the patient support surface.

In accordance with an alternative aspect of the invention, there is provided a radiation treatment support platform having (i) an opening to allow a woman's breast to hang down through the opening and below the treatment support platform to receive radiation when a woman is placed on the patient support surface in a prone position; (ii) a plurality of connectable platform sections such that the opening may be placed on either the right or the left side; and (iii) a material which deforms reproducibly and repeatedly returns to its original shape (memory foam) adjacent to at least one surface of the platform sections to allow reproducibility of the patient's position.

These and other aspects, features, and advantages of the present invention will be apparent from the accompanying Drawings and Description of the Preferred Embodiment.

BRIEF DESCRIPTION OF THE DRAWINGS

FIG. 3b is a side view of the radiation treatment table shown in FIG. 3a;

FIG. 4b is a side view of the radiation treatment table shown in FIG. 4a;

FIG. 5b is a side view of the radiation treatment table shown in FIG. 5a;

FIG. 6b is a side view of the radiation treatment table shown in FIG. 6a;

FIG. 7b is a side view of the radiation treatment table shown in FIG. 7a;

FIG. 8b is a side view of the head positioning device shown in FIG. 8a;

FIG. 9b is a side view of the head positioning device shown in FIG. 9a;

FIG. 10b is a side view of the head positioning device shown in FIG. 10a;

FIG. 11b is a side view of the head positioning device shown in FIG. 11a;

FIG. 12b is a side view of the head positioning device shown in FIG. 12a;

DETAILED DESCRIPTION OF THE PREFERRED EMBODIMENT

Figure 1:
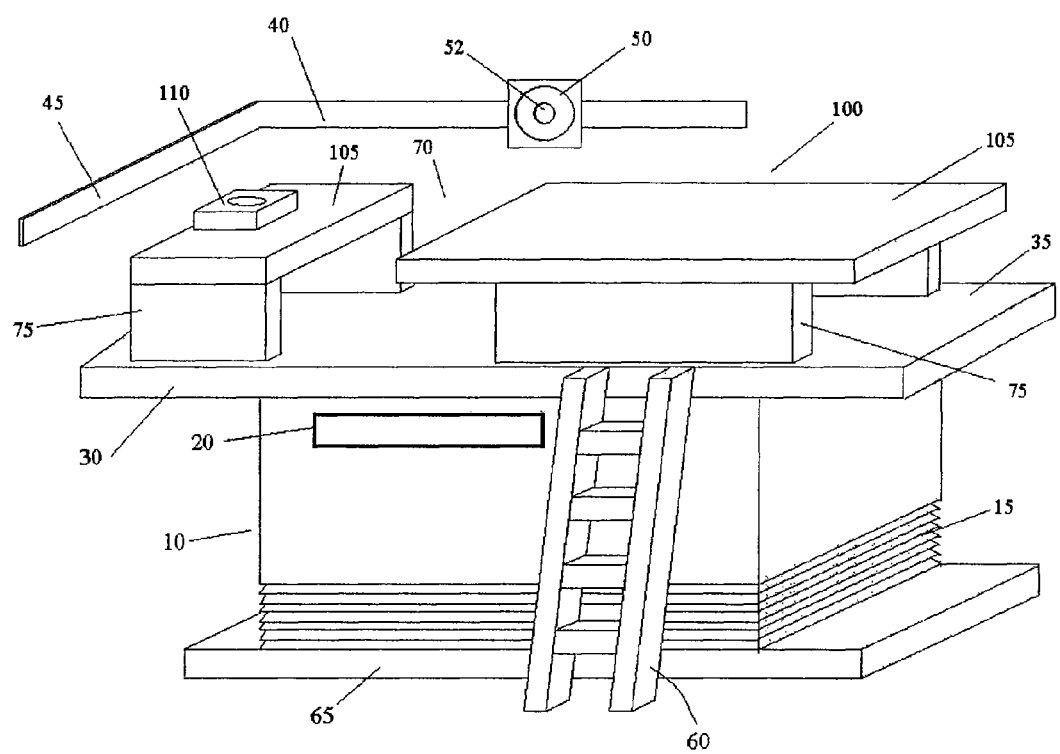
FIG. 1 is a perspective view of a radiation treatment table in conjunction with a radiation accelerator table and a linear accelerator machine in accordance with the present invention.
Figure 2:
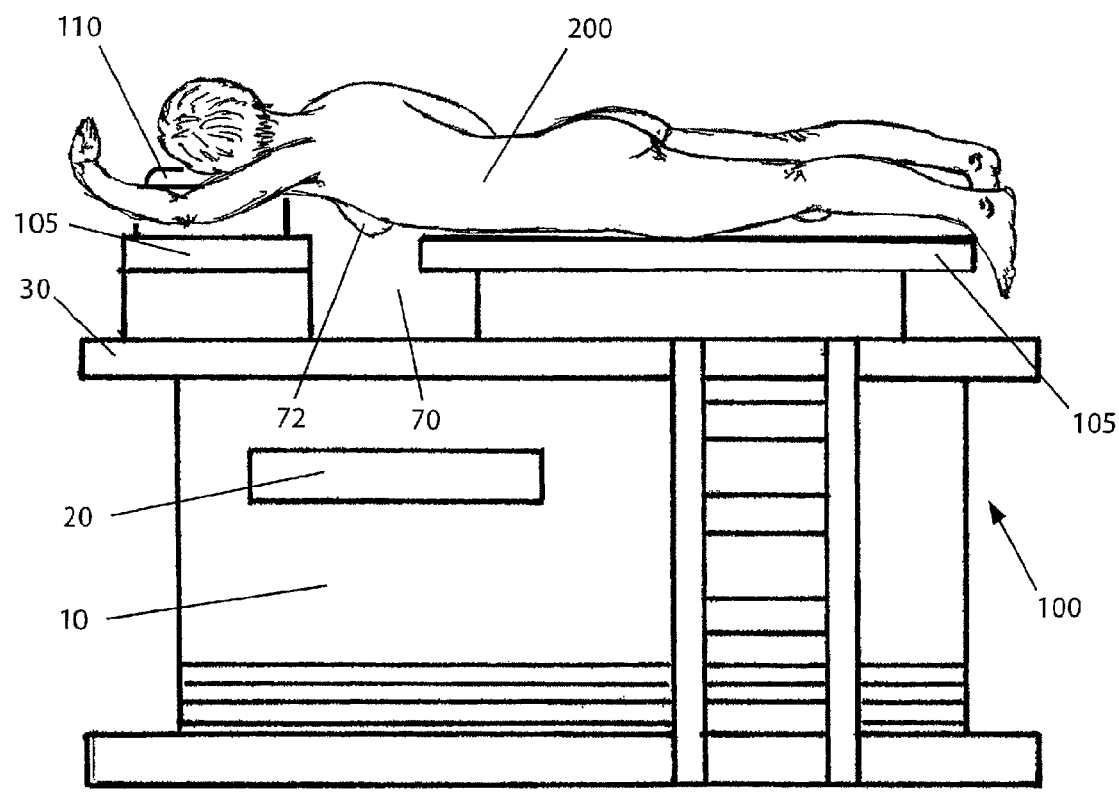
FIG. 2 is a side view of a radiation treatment table placed on a radiation accelerator table, with a female patient in a prone position on the treatment table in accordance with the present invention.

By way of overview and introduction, the method and radiation treatment table for prone patient positioning according to the present invention can be used with conventional linear accelerator machines and radiation accelerator tables. As shown in FIGS. 1 and 2, the treatment table 100 is placed upon a conventional accelerator table (shown generally as 10). Conventional accelerator tables have a top surface 35 with dimensions typically on the order of 2 meters.

Preferably, the treatment table 100 of the present invention is securely positioned upon and supported by the accelerator table 10. The treatment table 100 may be attached to the top surface 35 or one of the side surfaces of the accelerator table 10. The treatment table 100 is preferably attached to the top surface 35 by one of a variety of ways, as discussed in more detail below. The treatment table 100 is constructed of suitable materials such that it will not interfere with the radiation and other imaging modalities with which it may be used. Preferably, the treatment table 100 does not contain metals that are known to interfere with such radiation and imaging systems.

Because the treatment table 100 has a patient support surface 105 that is elevated above the top surface 35 of the accelerator table 10, a ladder 60 may be provided to enable a patient to climb up to the patient support surface 105. Alternatively, other ways of enabling a patient to reach the patient support surface 105, such as by providing an upper level entrance, may be used.

The treatment table 100 includes a generally horizontal patient support surface 105 that is elevated above the surface 35 of accelerator table 10. The patient support surface 105 shown in FIGS. 1 and 2 has a generally rectangular cross-section area; however, it will be appreciated that any shaped cross-sectional area may be used. The patient support surface 105 incorporates various ergonomic principles to enhance patient comfort, such as the use of padding placed atop the patient support surface 105. The extent of the elevation of the patient support surface 105 is determined by the height chosen for the vertical support walls of the platform support 75 as described below. Specifically, the patient support surface 105 should be at a sufficient height to accommodate various sizes of patient's breasts that will hang dependently below an opening 70 in the patient support surface. Preferably, the height should be selected to be great enough such that the breast sizes typically encountered would not touch the top surface 35 when hanging from the patient support surface 105.

Preferably, a patient's breast is positioned to freely suspend through the opening 70 such that it is not in contact with either the treatment table 100 or top surface 35 of the accelerator table 10. This configuration optimizes the shape and positioning of the breast for isolated radiotherapy without interference from the surrounding apparatus or the chest wall. This configuration also allows the clinically determined medial and lateral aspects of the breast tissue to be included within the projection of radiation portals emitted from accelerator head 52 at a treatment area below the opening 70 and through the vertical supports 75. Irradiation of breast tissue while in the prone position also provides numerous benefits as discussed above. Most importantly, by having the breast hang freely, the breast surface area available for treatment is increased, hot spots are minimized, radiation exposure of surrounding areas is minimized, and treatment results are accordingly improved.

As shown in FIGS. 1 and 2, the treatment table 100 may include two or more separate horizontally displaceable patient support surfaces (each of the two surfaces in FIG. 1 are shown as 105), each with its own platform support 75. Regardless of whether a unitary patient support surface 105 or multiple patient support surfaces 105 are used, the support surface 105 includes an opening 70 through which a breast 72 of a female patient 200 may dependently hang when the patient 200 is placed in a prone position atop the patient support surface 105. In this manner, the patient's breast 72 can hang beneath the patient support surface 105 and above the surface 35 of the accelerator table to receive imaging or treatment. It will be appreciated by those skilled in the art that various types of openings 70, as discussed in more detail below, may be used with the treatment table 100.

Treatment table 100 further includes a head positioning device 110 for comfortably and reproducibly supporting and positioning a patient's head while in the prone position. The head positioning device 110 may be moveably or fixably attached to the patient support surface 105 in any of a variety of ways as discussed below. The head positioning device 110 may be supported on top of the patient support surface 105 or may be elevated above the patient support surface as discussed below.

The accelerator table 10 shown in FIG. 1 includes a 360 degree horizontal swivel adjustable base 65, a vertically adjustable supporting frame 15, a horizontally adjustable table top 30, a control panel 20 which can be incorporated within the table top 30 or within the supporting frame 15 as shown, and a patient supporting surface 35 operatively connected to the horizontal plane adjustment mechanism of table top 30.

The treatment table 100 is shown in FIG. 1 positioned upon an accelerator table 10 which is in an operative arrangement with an accelerator machine, indicated generally as 45. The accelerator machine 45 used in connection with this invention may be of the vertically mounted 360 degree rotatable type as shown. Accelerator machines of this type consist basically of a vertical floor mounted stand (not shown) and an accelerator head supporting arm 40 pivotably axially mounted upon the stand and having a right angle bend to allow 360 degree positioning in a vertical plane of the beam emitting face 52 of accelerator head 50, mounted at an end of supporting arm 40, about the patient supporting surface 35 of accelerator table 10. With the treatment table 100 positioned upon the patient supporting surface 35 of accelerator table 10 as described, the 360 degree rotatable accelerator head 52 can be positioned at all points radially in a vertical plane about the patient. By horizontal rotation of accelerator table base 65 as indicated, the position of the patient and platform can be adjusted in a horizontal plane relative to accelerator head 52. Thus, all of the vertical and horizontal adjustments of the accelerator machine 65 relative to accelerator table 10 can be made with the treatment table 100 in position upon the accelerator table 10 as shown.

Moreover, a breast suspended from a prone position through an opening 70 in treatment table 100 can be irradiated, without any obstruction or interference from the treatment table 100 and the patient supporting surface 35 of accelerator table 10, from all positions of adjustment of the accelerator head 52 relative to accelerator table 10. It will further be appreciated that the method and apparatus of this invention can be used with any suitable source of radiation which can be suitably positioned to direct radiation beams to the treatment field of the platform in portals of suitable geometry as described.

As shown in FIGS. 3a-7b, the treatment table 100 includes a patient support surface 105 having an opening 70 through which a female patient's breast may hang dependently beneath the patient support surface 105. Preferably, the patient's breast may hang freely through the opening 70 without interference from any of the sides of the opening 70. Opening 70 may also be padded to enhance patient comfort. Opening 70 may take any of a variety of forms and shapes so long as a sufficient area for the hanging breast is provided.

Figure 3A:
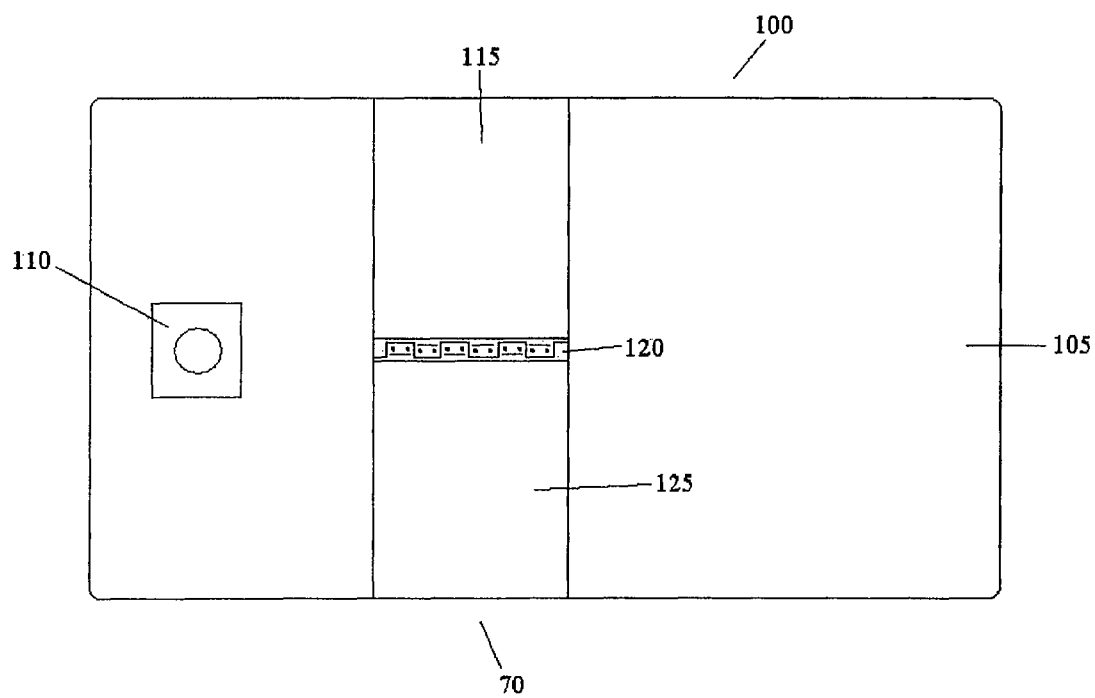
FIG. 3a is a top view of an embodiment of a radiation treatment table in accordance with the present invention.
Figure 3B:
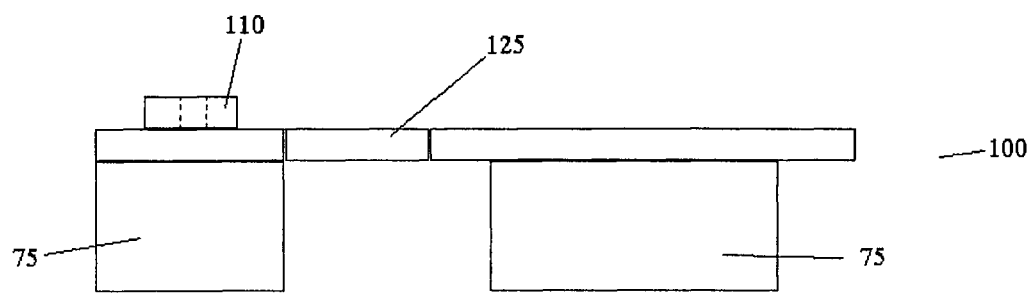

As shown in FIGS. 3a-b, one type of opening may be formed using a hinged mechanism 115/120/125 included with the top surface 105. The hinged mechanism includes a left breast panel 125, a right breast panel 115 and a hinge 120 such that either of the right or left breast panels 115/125 may rotate around the hinge to the other side to form an open area in the other side of the top surface 105 through which a breast may fall. For example, when the left plate 125 is rotated around the hinge, it may rest on top of the right plate 115 and form an open area through which the patient's left breast may dependently hang. Similarly, the right plate 115 may operate to rest on the left plate 125 and allow the right breast to hang. Therefore, either the left or right breasts can be easily placed through their respective openings to receive treatment and/or therapy. The size of the left and right breast plates 115/125 may be selected to accommodate the largest size breast typically encountered; alternatively, different sized breast plates 115/125 may be interchangeably attached to and used with hinge 120. An advantage of this mechanism is that only the breast to be treated is exposed to radiation, while the other breast is shielded by a breast panel.

Figure 4A:
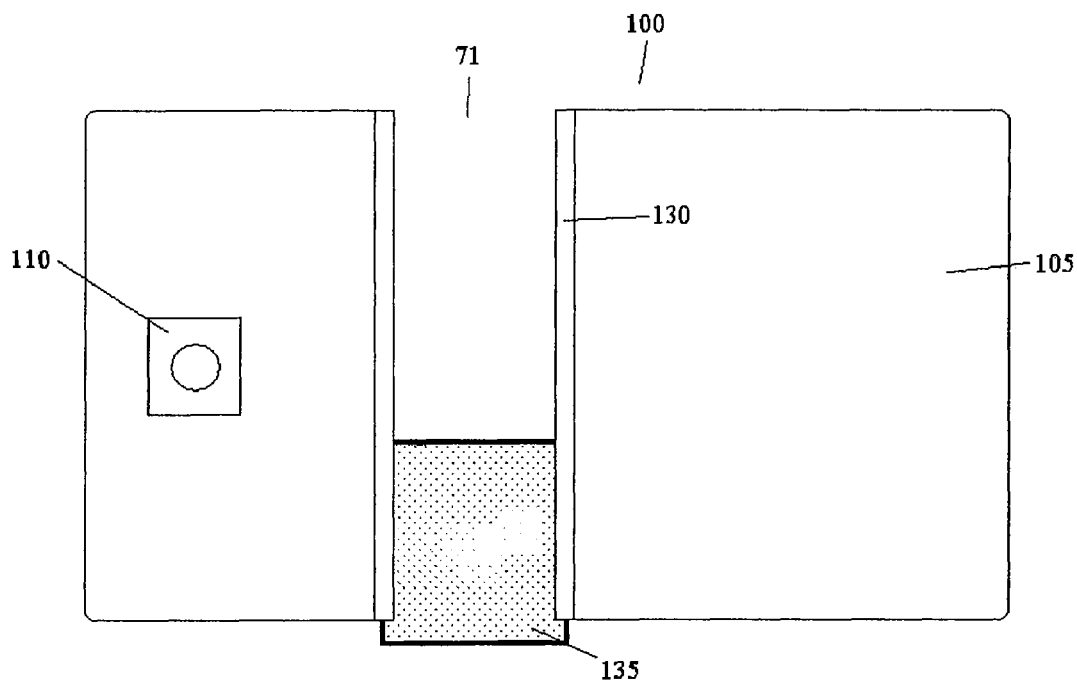
FIG. 4a is a top view of an alternative embodiment of a radiation treatment table in accordance with the present invention.
Figure 4B:
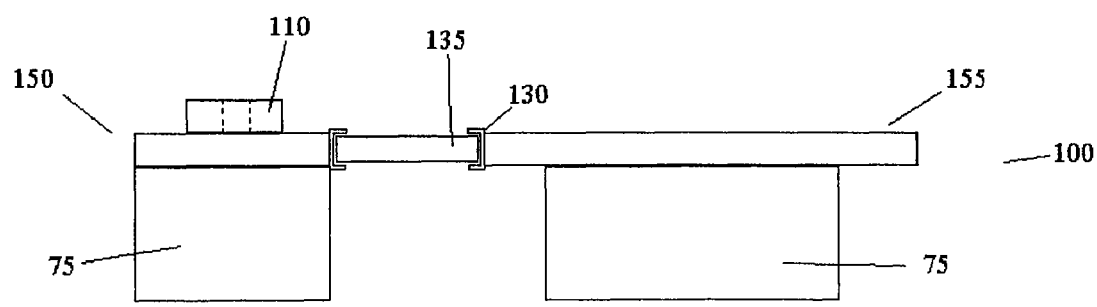

According to another embodiment shown in FIGS. 4a-b, an interior opening 71 is formed in the top surface 105. The opening 71 includes grooves 130 such that a removable breast plate 135 can slide within the grooves 130 to cover all or part of the opening 71. The plate 135 fits substantially flush with the top surface 105. In this way, either the left or right side of the top surface 105 can be covered while the other side remains open. Thus, one breast can be supported by the plate 135 while the other breast dependently hangs through the opening 71. It can be seen that the plate 135 can easily move from one side of the top surface 105 to the other such that either breast can receive treatment and/or therapy. It is easily seen that the size of the opening 71 can be controlled to accommodate different breast sizes and is a function of the size and shape chosen for the plate 135. Plate 135 may be constructed in any size or shape such that it is connected to and substantially flush with the top surface 105. Additionally, plate 135 may be constructed from the same materials as top surface 105 or from some other material. According to one embodiment, the plate 135 is constructed of a suitable transparent material to allow for visual verification of the breast position and the anterior chest wall through the opening 71 and the top surface 105.

While the opening 71 has been described as including a grooved surface with which mated grooves formed in the plate 135 interact to allow the plate 135 to slide, alternatively, plate 135 can move across the top surface 105 using pins and connectors or any other method for connecting two pieces as is known in the art.

Figure 5A:
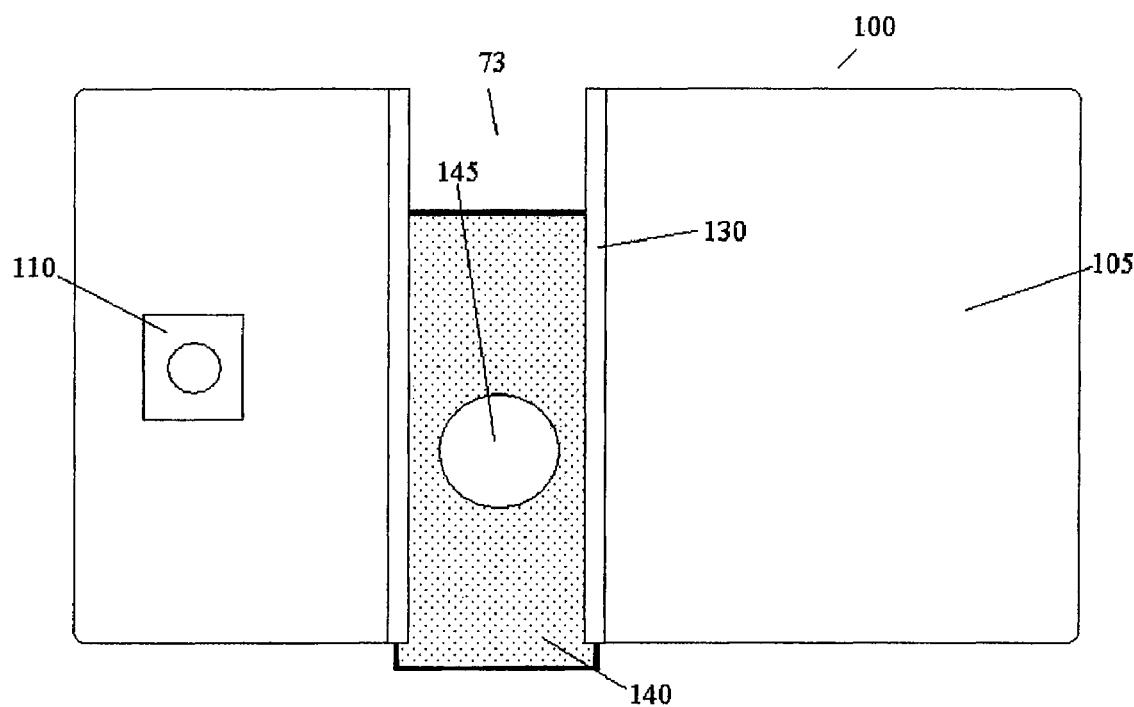
FIG. 5a is a top view of an alternative embodiment of a radiation treatment table in accordance with the present invention.
Figure 5B:
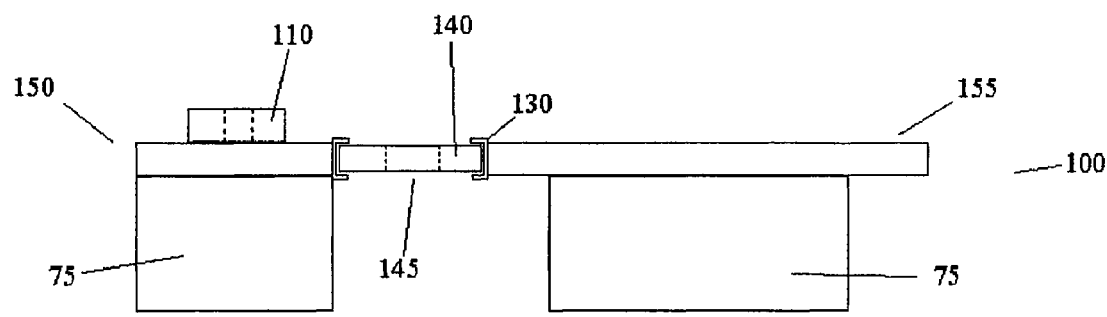

Another embodiment 73 is shown in FIGS. 5a-b. This embodiment is similar to the one illustrated in FIGS. 4a-b except that the slideable plate 135 in FIGS. 4a-b is replaced with a longer slideable plate 140 having a length approximately equal to the width of top surface 105. Further, plate 140 includes a breast opening 145 formed in either the left or right side of the plate such that either the left or right breast may dependently hang. Different plates 140 having holes 145 on different sides can be used for treating the right and left breast, respectively; alternatively, a plate 140 having two holes, one for each breast, can be used. Additionally, plates 140 having different sized holes 145 for different sized breasts may be interchangeably used. The plate 140 preferably includes contoured padding, such as foam or plastic, in the area of the hole 145 for providing patient comfort and to properly position the patient to optimize the morphology of the breast positioned through the hole 145.

As in the embodiment shown in FIGS. 4a-b, the plate 140 may be slideable within the top surface 105. Preferably this is accomplished by way of grooves formed in the opening 130 and similar mating grooves formed in the plate 140. Alternatively, any other way of connecting the top surface 105 and the plate 140 may be used.

Figure 6A:
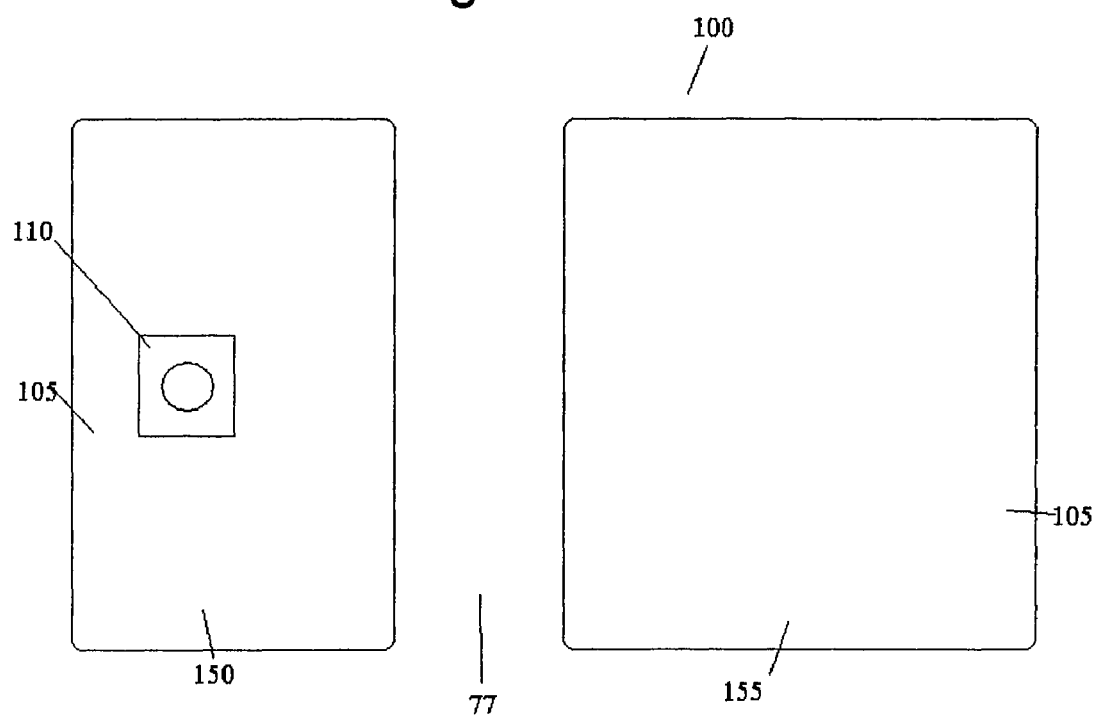
FIG. 6a is a top view of an alternative embodiment of a radiation treatment table in accordance with the present invention.
Figure 6B:
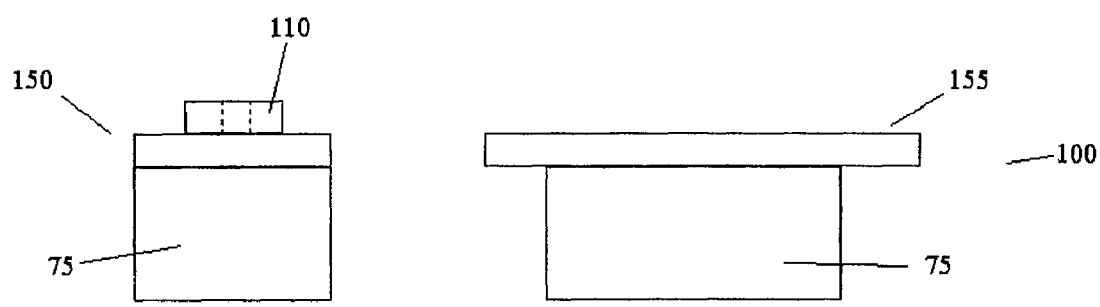

In an alternative embodiment shown in FIGS. 6a-b, the top surface 105 includes a front portion 150 and a back portion 155 that are separately formed. Preferably, the front and back portions 150/155 are of similar height such that a patient can be supported using both surfaces at an even height. The front and back portions 150/155 are moveable relative to one another along a substantially planar surface such that an opening 77 of variable size can be formed between the two surfaces 150/155 by moving one or both of the portions relative to the other as necessary. It can be seen that various sizes of openings 77 for different sized breasts can thus be formed. It can also be seen that both breasts, rather than just a single breast, would dependently hang through the opening 77 in this embodiment. For this reason, the breast not receiving treatment and/or therapy and the surrounding areas would need to be isolated and protected as is known in the art.

Figure 7A:
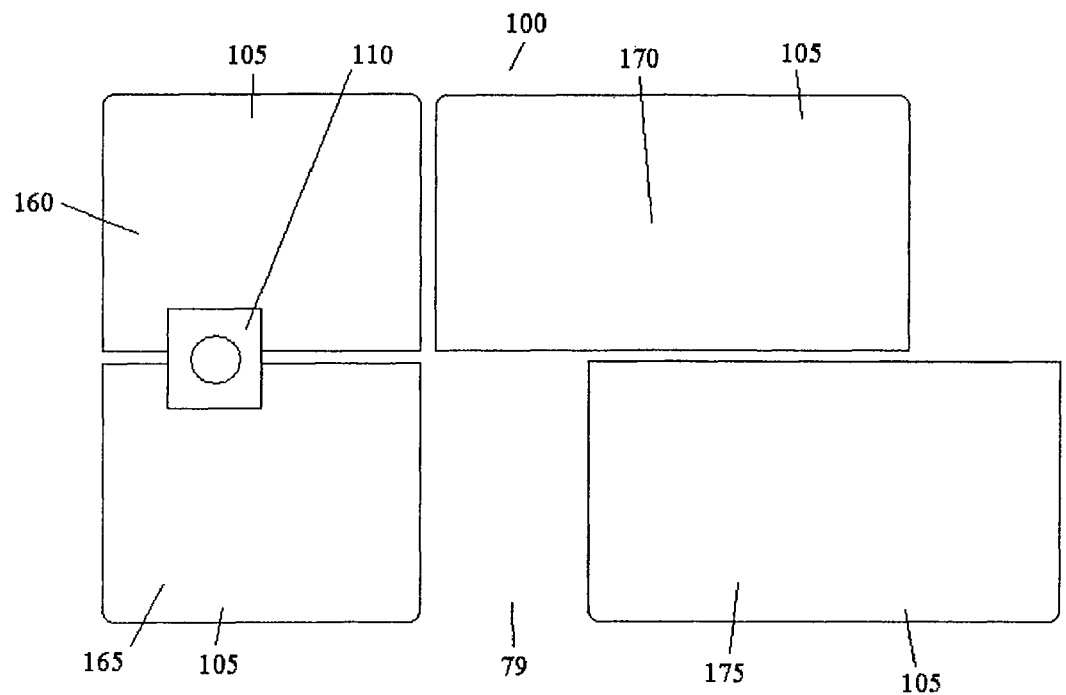
FIG. 7a is a top view of an alternative embodiment of a radiation treatment table in accordance with the present invention.
Figure 7B:
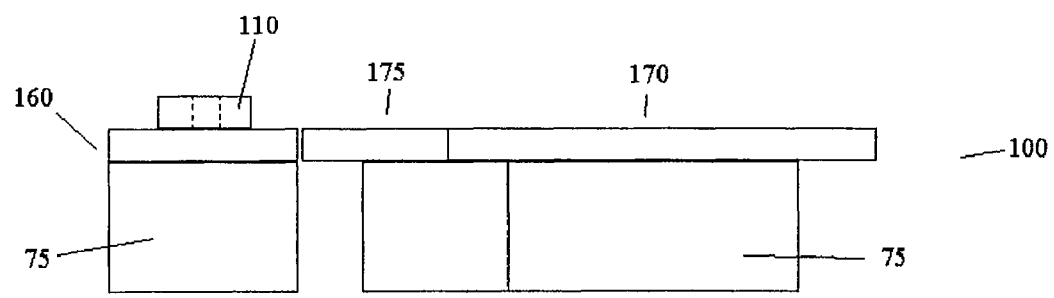
Figure 8A:
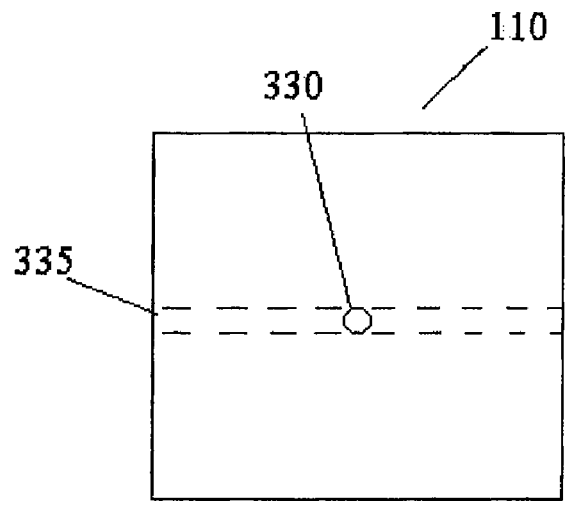
FIG. 8a is a top view of one embodiment of a head positioning device in accordance with the present invention.
Figure 8B:
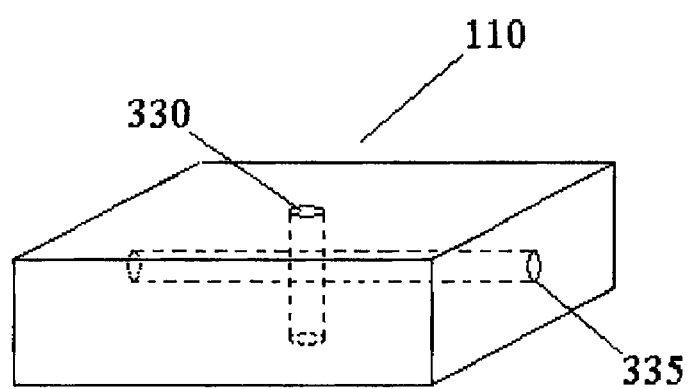
Figure 9A:
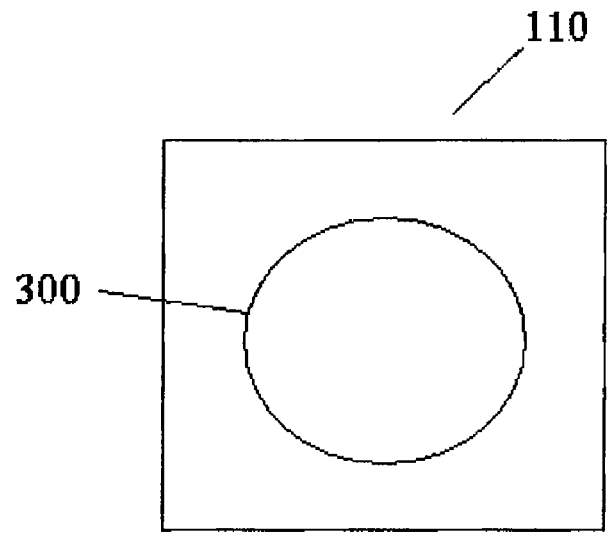
FIG. 9a is a top view of an alternative embodiment of a head positioning device in accordance with the present invention.
Figure 9B:
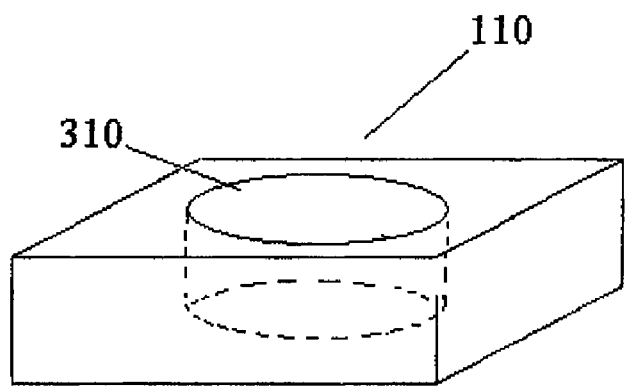
Figure 10A:
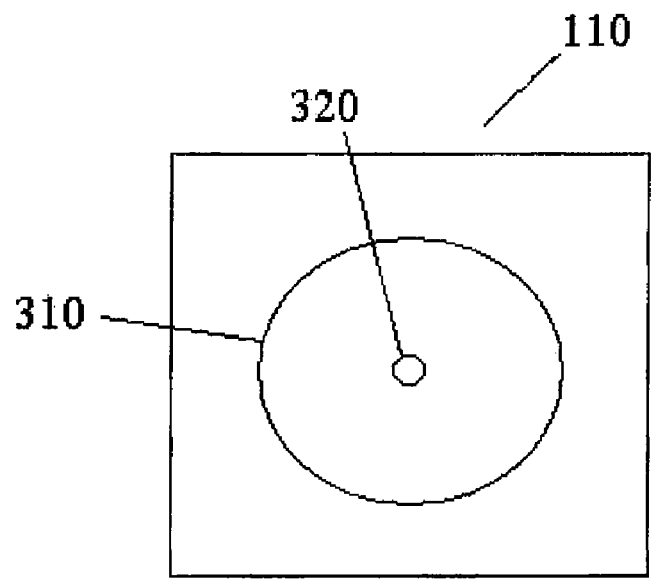
FIG. 10a is a top view of an alternative embodiment of a head positioning device in accordance with the present invention.
Figure 10B:
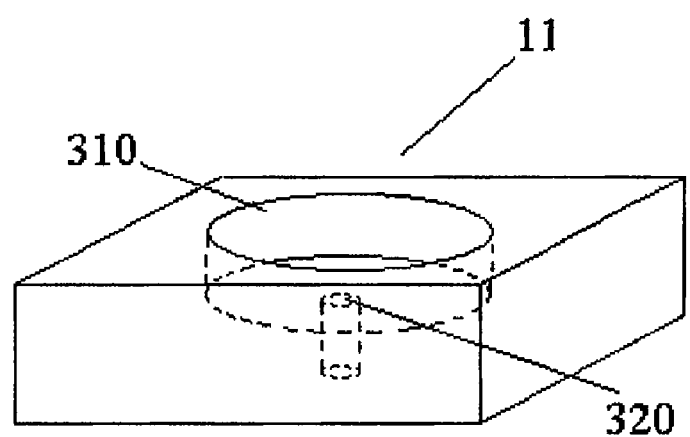

Yet another embodiment is shown in FIGS. 7a-b. This embodiment is similar to the one shown in FIGS. 6a-b except that the back side 155 in FIGS. 6a-b has been replaced by a left back side 175 and a right back side 170, and the front side 150 in FIGS. 6a-b has been replaced by a left front side 165 and a right front side 160. Alternatively, a unitary front side 160/165 can be used in conjunction with the separate sided back side 170/175. Either or both of the left and right back sides 170/175 can be moved relative to their respective front side 160/165 to create an opening for one or both of the breasts. For example, to treat only the left breast, the right back side 170 can be placed near the right front side 160 and the left back side 175 can be spaced apart from the left front side, such that the right breast can be supported and the left breast can dependently hang through the opening 79 formed by the gap to receive treatment and/or therapy. Alternatively, the right breast can be made to dependently hang in the same manner.

As shown in FIGS. 8-12, the treatment table 100 also includes a head positioning device 110. The head positioning device supports the patient's head while in the prone position and enables the patient's breasts to be repeatedly and reproducibly positioned in the opening, e.g. opening 70. The head positioning device 110 is attached to the treatment table 100 in a fixed position. By positioning the patient's head in a fixed position with respect to the treatment table 100, it necessarily follows that the patient's breast will also be positioned in a fixed, reproducible position for every treatment.

Figure 11A:
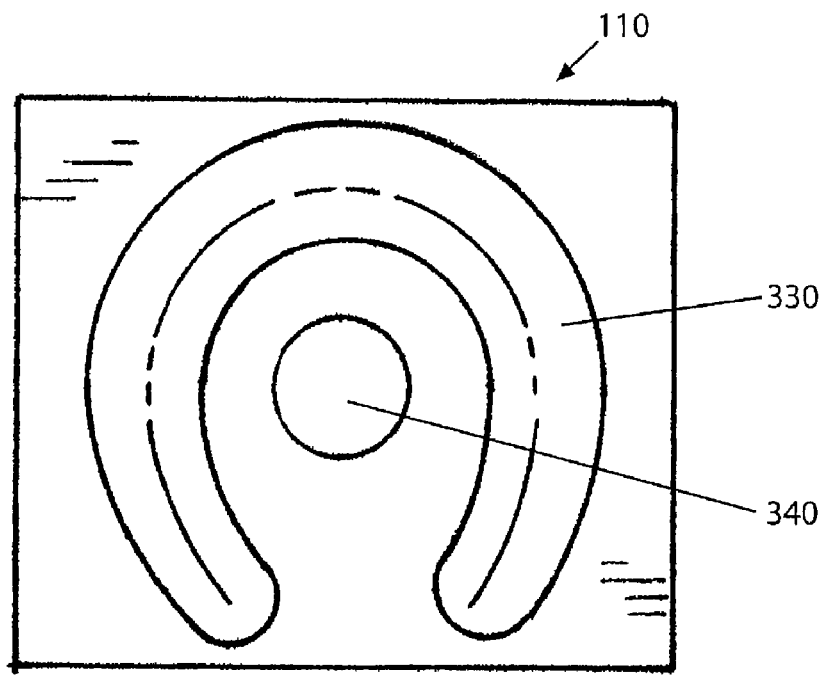
FIG. 11a is a top view of an embodiment of a head positioning device having a head cushion in accordance with the present invention.
Figure 11B:
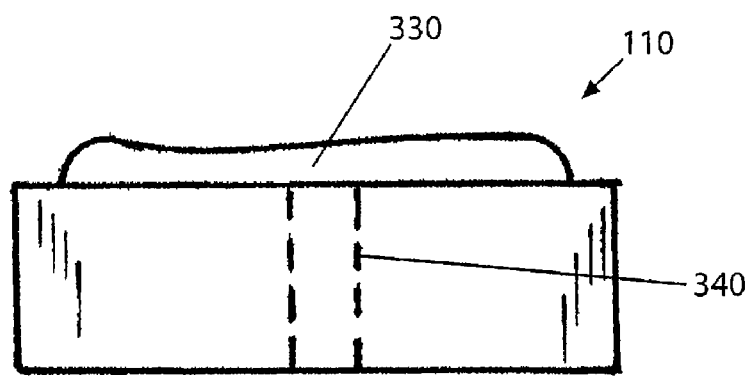

The head positioning device 110 may be constructed of foam or memory foam, molded plastic, or any of a variety of materials as are known in the art. The advantage of memory foam is that a single head positioning device 110 may be used for several patients. For each patient, their particular head shape and weight will create a particular and reproducible impression in the foam. In between patients, the memory foam will return to its original shape and will be ready for another imprint. The advantage of molded plastic is that it can be customized for, and maintained by each individual patient. The head positioning device 110 may also include a cushion 330/360 in a variety of shapes and sizes for patient comfort and to further aid in patient positioning as shown in FIGS. 11-12.

Figure 12A:
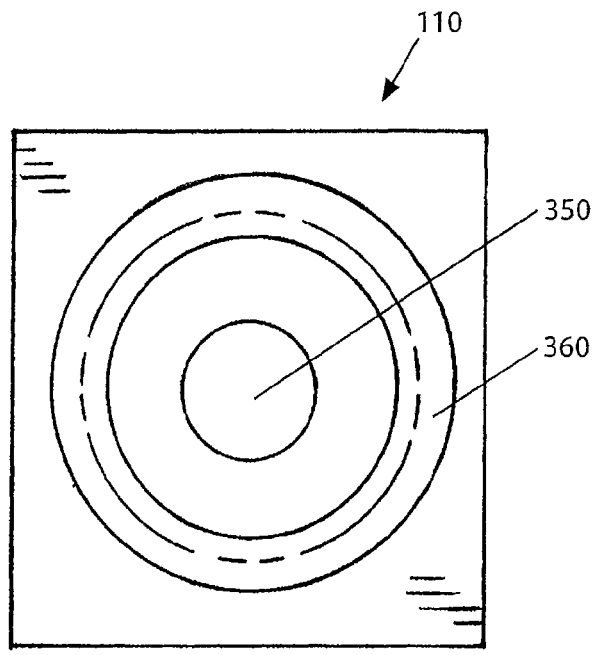
FIG. 12a is a top view of an embodiment of a head positioning device having a head cushion and an elevation support in accordance with the present invention.
Figure 12B:
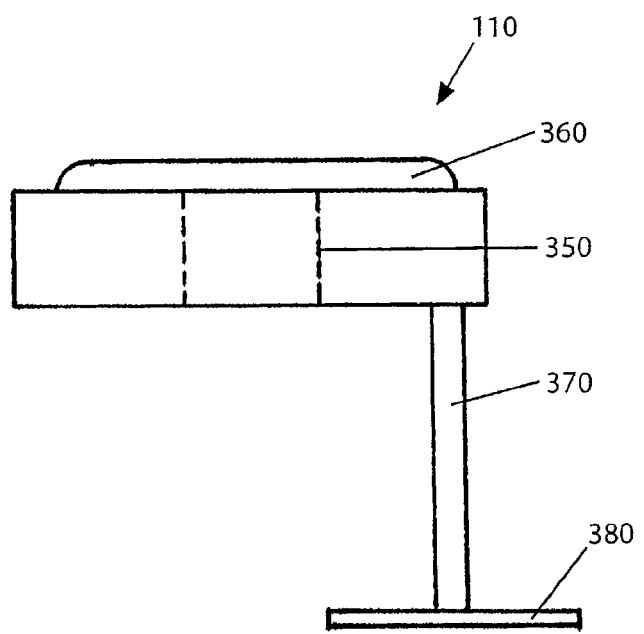

The head positioning device 110 is secured to the top surface 105 of the treatment table 100. According to one embodiment, the head positioning device 110 is moveable with respect to the top surface 105 to position the head positioning device 110 relative to the breast opening 70. According to another embodiment, the head positioning device 110 is attached to the top surface 105, such as by screws, rods, pins or like methods of attachment. According to another embodiment, the head positioning device 110 is secured to the top surface 106 using Velcro®. According to yet another embodiment, as shown in FIGS. 12a-b, the head positioning device 110 is elevated above the patient support surface 105 using an upright support 370 and base mechanism 380. Preferably, the upright support 370 is adjustable to support a patient's head at a variety of different heights.

Preferably, the head positioning device 110 includes a generally circular opening 300 (although other shaped openings may also be used) extending through the head positioning device 110 for accommodating the patient's head. The opening may extend partially (310 in FIGS. 10a-b) or fully (300 in FIGS. 9a-b) through the head positioning device 110. Additionally, the head positioning device may include one or more air holes 330/335/320/340/350 to help the patient breath while in the prone position as shown in FIGS. 8-12. According to another embodiment, the head positioning device 110 may include a plurality of positioning areas for a patient's head, such as a left side head positioning area in which a patient's head is placed when treating the left breast, and a right side head positioning area in which a patient's head is placed when treating the right breast.

As shown in FIGS. 1-2 and again in FIGS. 3a-7b, the treatment table 100 includes a top surface 105 that is elevated above the top surface 35 of the accelerator 10 using a platform support 75 having substantially vertical support walls. The vertical support walls can be, for example, attached perpendicularly along the periphery of the patient support surface 105. Four support walls can be used at each corner of the patient support surface 105, or, alternatively, an extended wall along each of the sides of the support surface 105, or along the front and back of the support surface 105 may be used.

The vertical support walls may include one or more windows through which lateral, tangential, and/or opposed radiation beams are directed to the breast positioned through opening 70. Alternatively, the radiation beams may be directed through openings formed between the support walls. Where windows are used, their size may be chosen to correspond to and in part define the desired size of a treatment field and the direction/deflection of the radiation beams passing therethrough.

The platform support 75 and vertical support walls can be made of any radiation compatible material having suitable weight-bearing strength. In one embodiment, the support walls can be made of or include portions made of transparent material to enable visual verification of the patient position within a treatment field and the position of a radiation source relative to one or more windows formed in the vertical support walls. According to one embodiment, the patient support surface 105 may include two or more separate surfaces (as shown FIGS. 6b and 7b), and each of the patient support surfaces 105 may include its own platform support 75.

An optimum height of the patient support surface 105 above the top surface 35 of the accelerator table 10 can be determined according to a mean average distance that a large or pendulous breast will hang through opening 70. A vertical clearance of approximately 30 centimeters is generally sufficient for most patients.

Figure 13:
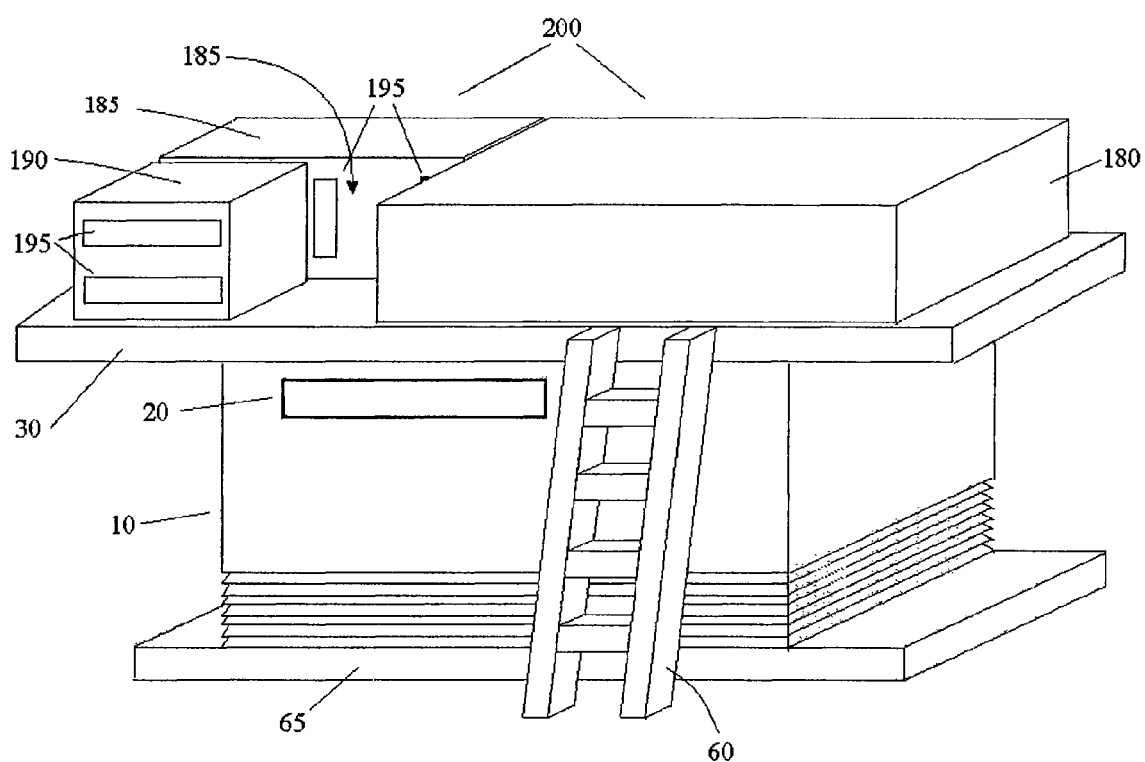
FIG. 13 is a perspective view of a radiation treatment platform in conjunction with a radiation accelerator table and a linear accelerator machine in accordance with an alternative embodiment of the present invention.

In another embodiment of the proposed invention, as shown in FIG. 13, a treatment support platform 200 may be used instead of the treatment table. The treatment support platform 200 is shaped such that an opening 81 is formed on one side. The treatment support platform 200 may be a single unit with a cutout section, or it may be made of several modular sections 180/185/190 as shown in FIG. 13. If the treatment support platform 200 is a single unit, it should preferably have a support surface 105 on both the top and bottom surfaces such that either breast may be accommodated depending on which surface is used. For example, if the left breast is treated, the treatment support platform 200 is positioned such that an opening 81 is on the left side. Alternatively, if the right breast is treated, the treatment support platform 200 is flipped so that the opening 81 is on the right side.

If modular sections 180/185/190 are used for the treatment support platform 200, a plurality of shapes may be used to create an opening 81 to accommodate the breast to be treated. Preferably, if modular sections 180/185/190 are used, they may be attached to one another using Velcro® 195, adhesive, straps, hooks, buckles or any method known in the art to temporarily attach two surfaces. In the preferred embodiment using modular sections, a single large rear section 180 is used to support the patients abdomen and lower body. The upper sections 185/190 are positioned to support much of the upper body, but still create an opening 81 to allow the breast to be treated to hang through the opening. A large rectangular section 185 may be positioned such that its short side abuts the short side of the rear section 180 and its long side is flush with long side of the rear section 180. A small rectangular section 190 may be positioned adjacent to the long side of the large rectangular front section 185 so that it is flush with the short side of the large rectangular front section 185 at the front end of the platform. In such an embodiment, the large rectangular front section 185 supports the alternate breast, one shoulder, and one side of the patient's head while the small rectangular front section 190 supports the other shoulder and the other side of the patient's head. In this embodiment the opening 81 is surrounded on three sides by the support platform sections 180/185/190 and the breast to be treated may dependently hang through the opening. Alternatively, the small rectangular front section 190 may be positioned adjacent to the rear section 180 and support the alternate breast while the large rectangular front section 185 may be placed adjacent to the small rectangular front section and support both shoulders and the head creating an opening between the large rectangular front section 185 and the rear section 180. Again the opening would be surrounded on three sides by the three support platform sections 180/185/190. In this embodiment the front support sections 185/190 may be positioned to accommodate either breast for treatment.

Figure 14:
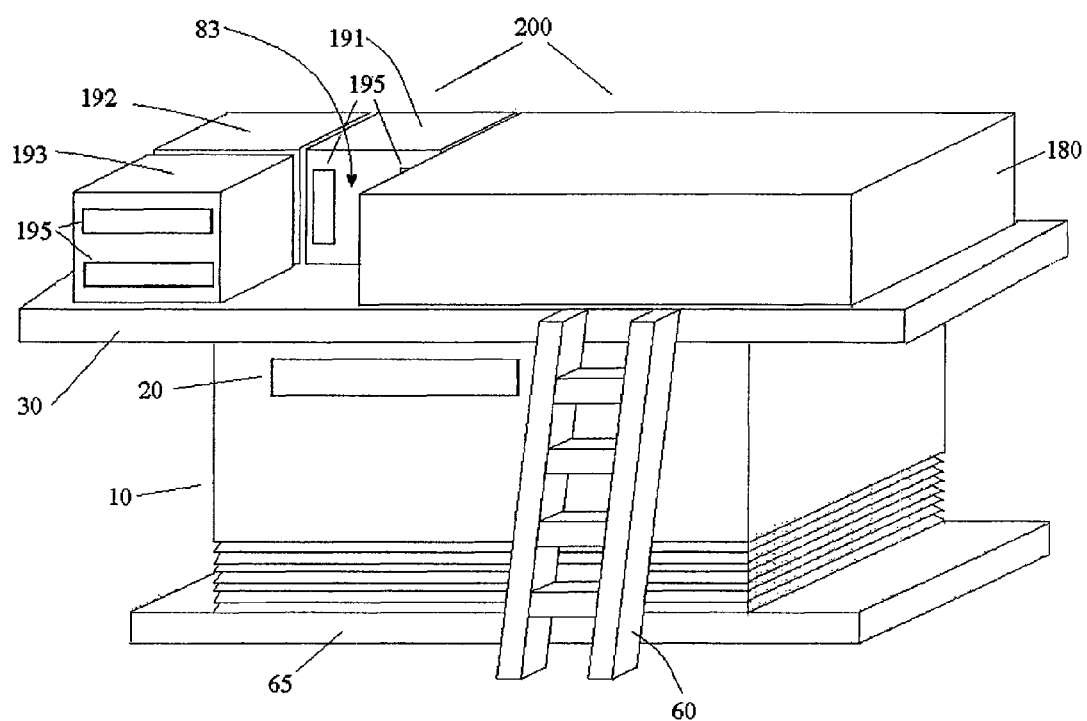
FIG. 14 is a perspective view of an alternative radiation treatment platform in conjunction with a radiation accelerator table and a linear accelerator machine in accordance with an alternative embodiment of the present invention.

In a similar embodiment, as shown in FIG. 14, three or more small sections 191/192/193 may be used to create the front side of the treatment support platform 200. The sections may be positioned such that there is an opening 83 for the breast to be treated but that the other parts of the body are supported by the treatment support platform 200. If three sections are used to create the front side of the support platform, one section 191 may be positioned such that one of its sides abuts the short side of the rear section 180 and an adjacent side is flush with the long the long side of the rear section. A second section 192 may be placed adjacent to the first section 191 and in front of the first section 191 and a third section 193 may be placed adjacent and next to the second section 191. In this embodiment the opening 83 would be surrounded on three sides by the rear section, the first front section and the third front section as mentioned above. As in the previous embodiment, either breast may be accommodated for treatment by changing the position of the front platform sections.

In yet another embodiment using modular sections, a single "L-shaped" front section may be used to support the patient's upper body. In this embodiment, the "L-shaped" section is placed so that the end of one leg of the "L-shaped" section abuts the short side of the rear section 180 and the long side of the "L-shaped" section is flush with the long side of the rear section 180. This provides an opening, through which the breast to be treated may hang, that is surrounded on two sides by the inside surfaces of the "L-shaped" section and on a third side by the rear section 180. The "L-shaped" section can accommodate either breast. For example, if the "L-shaped" section is placed to accommodate the right breast for treatment, it may be rotated about a vertical axis or flipped over such that the opening 70 moves to the other side of the support platform. If the "L-shaped" section is to be flipped to accommodate either breast both the top and bottom surfaces of the "L-shaped" section should be designed to provide appropriate padding for the patient.

While the invention has been described in connection with certain preferred embodiments thereof it is not limited to such embodiments but rather is defined by the scope of the claims appended hereto.

I claim:

1. A radiation treatment table comprising:
   a generally flat patient support surface, the surface comprising an opening to allow a woman's breast to hang downwardly through the opening and below said patient support surface to receive radiation when a woman is placed on said patient support surface in a prone position;
   a platform support connected to the patient support surface, the platform support comprising at least one vertical support, the at least one vertical support having an upper end coupled to the patient support surface and having a lower end adapted to be secured to a linear accelerator table; and
   a head positioning device attachable to the patient support surface.

2. The radiation treatment table of claim 1, wherein the head positioning device is moveable along the patient support surface.

3. The radiation treatment table of claim 1, wherein the head positioning device is fixably attached to the patient support surface.

4. The radiation treatment table of claim 1, wherein the head positioning device is constructed of molded plastic.

5. The radiation treatment table of claim 1, wherein the head positioning device is constructed of memory foam.

6. The radiation treatment table of claim 1, wherein the head positioning device further includes a cushion for a patient's head.

7. The radiation treatment table of claim 1, wherein the patient support surface further includes a padded upper surface.

8. The radiation treatment table of claim 1, wherein the patient support surface further comprises at least two generally flat support surfaces moveable relative to one another.

9. The radiation treatment table of claim 8, wherein the opening is formed between the at least two generally flat support surfaces.

10. The radiation treatment table of claim 1, wherein the opening is adjustable so as to accommodate different sized breasts.

11. The radiation treatment table of claim 1, wherein said opening is formed as part of a hinged opening plate.

12. The radiation treatment table of claim 1, wherein said opening is formed as part of a removable plate having a generally circular opening.

13. A method for reproducibly positioning a patient to receive radiation of the breast comprising the steps of:
    positioning a patient in a prone position upon a positioning platform, the positioning platform including a patient support surface elevated above a linear accelerator table, the patient support surface having at least one opening through which a breast may hang downwardly toward the linear accelerator table, the positioning platform further including a platform support having at least one vertical support having a lower end adapted to be secured to the linear accelerator table and having an upper end secured to the patient support surface, and a head positioning device;
    placing the patient's head in the head positioning device such that at least one of the patient's breasts is positioned to hang downwardly through the opening and below said patient support surface to receive radiation;
    positioning a radiation source relative to the patient's breast; and
    irradiating the breast.

14. The method of claim 13, further comprising the step of positioning the opening to allow the at least one breast to hang freely through the opening.

* * * * *